(12) United States Patent
Raspopovic et al.

(10) Patent No.: US 10,974,043 B2
(45) Date of Patent: Apr. 13, 2021

(54) INTRAFASCICULAR ELECTRODE IMPLANT

(71) Applicant: ECOLE POLYTECHNIQUE FEDERALE DE LAUSANNE (EPFL), Lausanne (CH)

(72) Inventors: Stanisa Raspopovic, Chavannes-Renens (CH); Francesco Maria Petrini, Lausanne (CH); Silvestro Micera, Geneva (CH)

(73) Assignee: ECOLE POLYTECHNIQUE FEDERALE DE LAUSANNE, Lausanne (CH)

( * ) Notice: Subject to any disclaimer, the term of this patent is extended or adjusted under 35 U.S.C. 154(b) by 40 days.

(21) Appl. No.: 16/332,161

(22) PCT Filed: Sep. 29, 2017

(86) PCT No.: PCT/IB2017/056008
§ 371 (c)(1),
(2) Date: Mar. 11, 2019

(87) PCT Pub. No.: WO2018/065868
PCT Pub. Date: Apr. 12, 2018

(65) Prior Publication Data
US 2019/0217083 A1 Jul. 18, 2019

Related U.S. Application Data

(60) Provisional application No. 62/403,727, filed on Oct. 4, 2016.

(51) Int. Cl.
*A61B 5/00* (2006.01)
*G16H 40/63* (2018.01)
(Continued)

(52) U.S. Cl.
CPC ........ *A61N 1/0556* (2013.01); *A61B 5/04001* (2013.01); *A61B 5/685* (2013.01); *A61B 5/6877* (2013.01)

(58) Field of Classification Search
CPC .. A61N 1/0556; A61B 5/04001; A61B 5/685; A61B 5/6877
See application file for complete search history.

(56) References Cited

U.S. PATENT DOCUMENTS

2008/0046055 A1 2/2008 Durand et al.
2012/0259388 A1 10/2012 Galvin-Garcia
(Continued)

FOREIGN PATENT DOCUMENTS

WO WO 01/22877 A1 8/2015

*Primary Examiner* — Michael W Kahelin
*Assistant Examiner* — George E Banis
(74) *Attorney, Agent, or Firm* — R. Neil Sudol; Henry D. Coleman

(57) ABSTRACT

An implantable device for intrafascicular stimulation and/or sensing of a peripheral nerve, including a blocking element adapted for wrapping a nerve, comprising an access point and an exit point, and an electrode adapted to traverse the blocking element via the access point and the exit point having a distal end, a proximal end and an elongated body in between, the electrode being electrically isolated from the surrounding environment except that for an active site. In another aspect, the invention features a system comprising the implantable device of the invention operably coupled with an external device such an electrostimulator and/or a sensing device for sensing and recording electrical nerve signals.

8 Claims, 3 Drawing Sheets

(51) Int. Cl.
*A61B 5/11* (2006.01)
*A61B 5/0205* (2006.01)
*A61B 5/021* (2006.01)
*A61B 5/024* (2006.01)
*A61M 1/10* (2006.01)
*A61M 1/12* (2006.01)
*A61N 1/05* (2006.01)
*A61B 5/04* (2006.01)

(56) References Cited

U.S. PATENT DOCUMENTS

2015/0141786 A1* 5/2015 Durand .............. A61N 1/0558
  600/377
2015/0216682 A1* 8/2015 Achyuta ............. A61N 1/0558
  607/118

* cited by examiner

INTRAFASCICULAR ELECTRODE IMPLANT

TECHNICAL FIELD

The invention relates to interfaces for establishing electrical contact with a living tissue, in particular it relates to an electrode implant for stimulation and/or sensing of a peripheral nerve and to its use, e.g. within a neuro-prosthesis.

BACKGROUND ART

A nerve is a cordlike structure conveying impulses between some part of the central nervous system and some other region of the body. A nerve is made of individual nerve fibers (axons) with their sheaths and supporting cells, small blood vessels, and a surrounding connective tissue sheath. Each nerve fiber is surrounded by a cellular sheath (neurilemma) from which it may or may not be separated by a myelin sheath). A group of such nerve fibers surrounded by a sheet of connective tissue (perineurium) is called a fasciculus. The fasciculi are then bound together by a thick layer of connective tissue (epineurium) to form the nerve.

Neurologists have long sought an electrode device which could establish stable mechanical and electrical contact with a large number of individual axons within a nerve. Such a device would find wide medical application for recording neurological impulses, facilitating the analysis and interpretation of such impulses, and delivering electrical stimuli to target nerve fibers as a reaction to such analysis or as a result of external input. The ideal electrode device would be adapted to the anatomy of the nerve so that it could penetrate the nerve in a non-destructive fashion in order to form focused electrical contacts with a very large number of individual nerve fibers.

Peripheral nerve interfaces (Navarro et al., *J. Peripher. Nerv. System*, 10, 229-258, 2005; Shultz and Kuiken, *PM&R*, 3.1, 55-67, 2011; Ciancio et al., *Frontiers in neuroscience*, 10, 2016) have been used to record signals from, and to inject electrical current in, the human nerves. Among these, FINE, CUFF, LIFE, TIME and Utah array electrodes have been used on humans.

The FINE or CUFF electrodes are stable (in terms of biocompatibility and functionality) in a long-term implant in the human nerves because they are placed totally around them. On the other side, they are not selective, exchanging information with more than a nerve fascicle at time. This implicates, e.g. in the case of sensory feedback restoration, that they can elicit a localized sensation without modulating its intensity (Badia et al., *J. Neural Eng.*, vol. 8, no. 3, 2011).

LIFE/TIME/Utah array on the other hand, are more selective and then allow transmission of gradual information, e.g. touch intensity. However, they are less stable. In particular, LIFE and TIME are constituted by a substrate of e.g. polyimide on which conductive material is printed. Their stability during long-term implants has not been proven yet. The implanting procedure, even though quite complicated, favours a stable mechanical connection between the electrodes and the nerve. Utah array electrodes are stable in the human body (proven through brain implants) but the implanting technique in a peripheral nerve is not efficient since the electrode can move once the surgery is over.

Several medical devices have exploited peripheral nerve interfaces for hand prosthesis movement control and sensory feedback restoration (Raspopovic et al., *Science translational medicine* 6.222: 222ra19-222ra19, 2014; Tan et al., *Science translational medicine*, 6 (257), pp. 257ra138-257ra138, 2014), bladder control (clinical practice), epilepsy/depression treatment (e.g. Cyberonics), foot drop treatment (e.g. Ottobock), sight restoration (e.g. Second Sight).

A plethora of documents describe peripheral nerve interfaces. For instance, U.S. Pat. No. 4,969,468 and WO2016005400 disclose a cuff interface that presents an array of spikes in the inner face. The cuff is used as a support for the spikes for stably inserting them in the nerve.

U.S. Pat. No. 5,634,462 describes a FINE electrode that, according to the configuration, shapes the nerve in different ways to maximize the selectivity of the interfacing with the nerve itself.

WO2012149039 and US2014128951 disclose an electrode constituted by a group of cables, each of which composed by a conductive material surrounded by an insulating sheath. The cables are inserted longitudinally in the nerve.

EP1726329 discloses a hermetically sealed three-dimensional electrode device particularly useful for neuron interface and more specifically as a cortical implant. It includes an assembly (array) of electrically conductive electrodes arising from a substrate where the electrodes are hermetically bonded to the substrate. The electrodes also include an insulating layer which leaves at least one zone or at least one hole exposed for making focused electrical contact with the tissue. One major problem with this implant, as for e.g. the Utah arrays, is its instability if used on a peripheral nerve and the need to establish in advance the length of each electrode needle, or the position of the electric reveal thereon, for an efficient tissue stimulation. A similar teaching is reported also in U.S. Pat. No. 4,969,468.

Despite a large amount of research and development performed in this field, there is still a need for an implantable device which guarantees a stable and durable bond with a peripheral nerve while assuring an efficient and selective electrical contact with single nerve fascicles.

SUMMARY

According to one aspect of the present invention, the drawbacks of the background art concerning both the stability and the efficacy of peripheral nerves' electrode interfaces is addressed and solved. A novel device is proposed that guarantee at the same time stimulation/sensing selectivity, mechanical stability with a nerve, and facility of implant.

The interface is mainly constituted by a blocking element adapted for wrapping a nerve and one or preferably a plurality (array) of elongated electrodes. The blocking element, which can be embedded as a cuff, is an insulating rigid or semi-rigid structure (e.g. shaped as a rectangular right prism) with an internal cavity where to place the nerve. This structure can be shaped as a single body element or can be constituted by at least two elements, which are joined with e.g. a hinge at one side and has on the other side a mechanism that allows them to be clicked together. Since the structure is substantially rigid, it shapes the nerve when it encloses it.

On at least two, usually opposed, portions or faces of the blocking element, one or a plurality of holes are present, through which elongated electrodes coated with an insulating material can be inserted. The insulating layer presents an active site, e.g. an isolation-free spot such as a through-hole or a stripe, which allows the electrical contact between the conductive material and the surrounding tissue, e.g. a nerve, once implanted. The electrodes are inserted through the cuff and the nerve so to contact the internal fascicles thereof. Once implanted, the electrodes can be fixed to the cuff to insure a long lasting coupling and secure the entire structure. The active site in the electrodes' insulating coating is put at different lengths on the different electrodes so to permit the connection with fascicles disposed at different profundities with respect to the surfaces of the cuff. Alternatively electrodes with active sites positioned at equal lengths are fixed in the cuff at different profundities to achieve the same result. Aside the holes array of the blocking element, two plates of conductive material are disposed. The electrodes can be used as both active sites and grounds, while the two plates have the function of ground.

The blocking element, once placed around a nerve, shapes it, in a way that does not allow relative motion between the two bodies. Thanks to this property, the electrical active sites maintain the same position in the nerve over time (promoting stability of the interfacing). A primary advantage of the present invention is therefore that it is easily installed on a nerve while providing improved intimate electrical and mechanical contact between the individual axons in the nerve bundle and at least one electrical energy conductive member.

The procedure of implant is facilitated by the electrode design: once the nerve is allocated in the cuff, the electrodes (embodied as e.g. needles or cables) are passed through the cuff itself and the nerve, and finally fixed through a mechanism on the cuff. At the same time, this setting grants a remarkable manufacturing advantage as well as a selectivity advantage: depending on the needs, the number of the electrodes can be chosen on a case by case basis so to reduce useless elements (thus also reducing the invasiveness of the device and therefore inflammatory reactions upon implant thereof in a subject), as well as the position of the active site on each electrode to precisely target specific fascicles without the need to previously shape each and any electrode in a fix implant.

Accordingly, another aspect of the present invention relates to an implantable device for intrafascicular stimulation and/or sensing of a peripheral nerve, characterized in that it comprises:

a) a blocking element adapted for wrapping a nerve, comprising an access point and an exit point; and b) an electrode adapted to traverse the blocking element via the access point and the exit point having a distal end, a proximal end and an elongated body in between, said electrode being electrically isolated from the surrounding environment except that for an active site.

In one embodiment, the active site is located along the elongated body.

In one embodiment, the active site is an isolation-free spot or a stripe.

In one embodiment, the blocking element is openable and closable.

In one embodiment, the electrode is a cable electrode.

In one embodiment, the device further comprises means for fixing the electrode to the blocking element.

In one embodiment, the active site can be displaced along the elongated body.

Yet another aspect of the present invention relates to a system for intrafascicular stimulation and/or sensing of a peripheral nerve comprising the above device operably connected with an electrical stimulator and/or an analyser.

DETAILED DESCRIPTION OF THE EMBODIMENTS

The present disclosure may be more readily understood by reference to the following detailed description presented in connection with the accompanying drawing figures, which form a part of this disclosure. It has to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a", "an" and "the" include plural referents unless the context clearly dictates otherwise. Thus, for example, reference to "an electrode" includes a plurality of such electrodes and reference to "an active site" includes reference to one or more active sites, and so forth.

Also, the use of "or" means "and/or" unless otherwise stated. Similarly, "comprise", "comprises", "comprising", "include", "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of".

The invention will now be described with the help of the following definitions and Figures.

Figure 1:
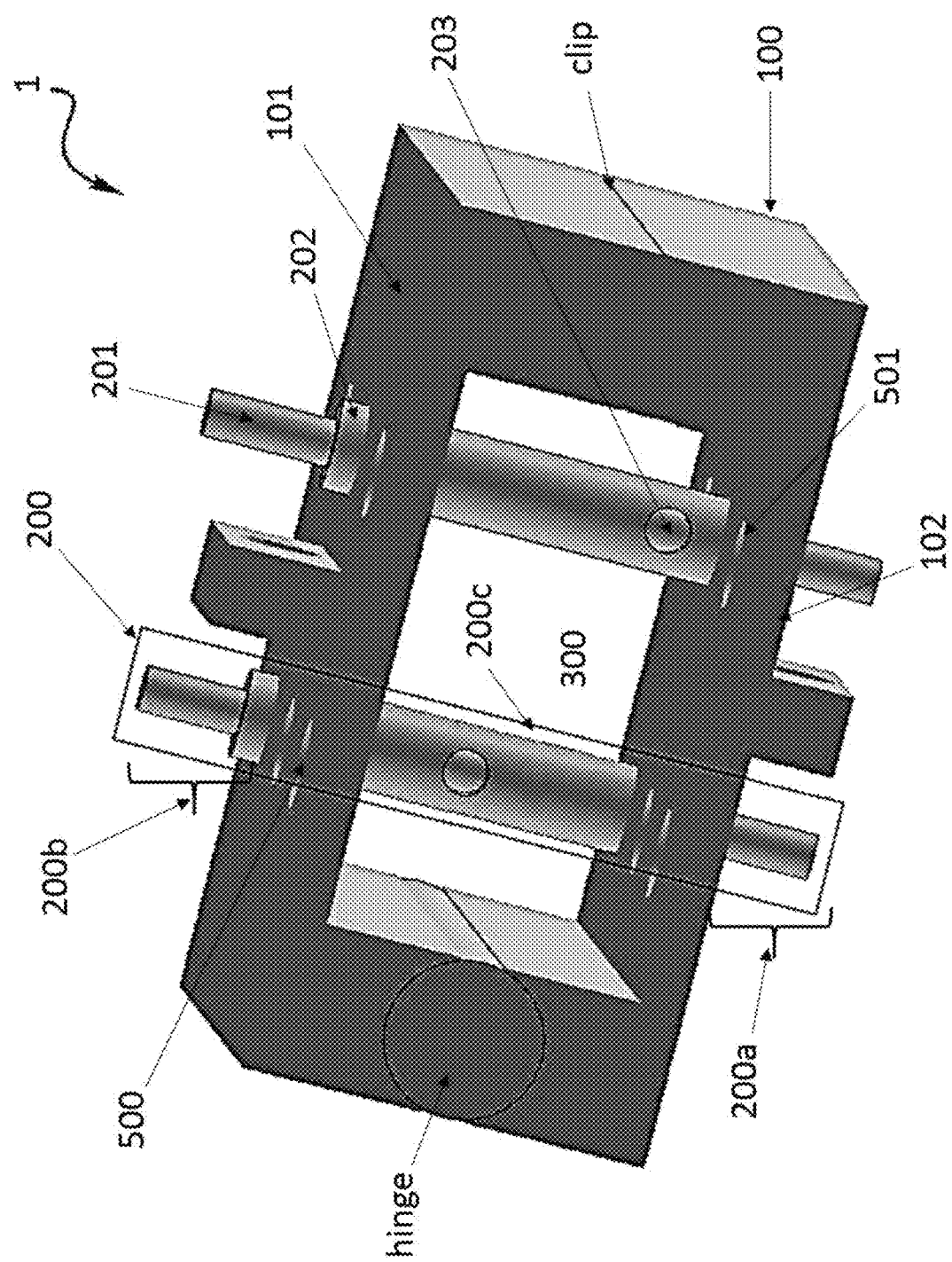
FIGS. 1 and 2 show one embodiment of the device according to an aspect of the invention.

With reference to FIG. 1, one non-limiting embodiment of the implantable device 1 according to one aspect of the invention is shown. In the depicted embodiment, a blocking element 100 for allocating a peripheral nerve is composed of two portions, defining an upper surface 101 and a bottom surface 102, which are opposed among them. The two portions are coupled on one side by a hinge 103 and on the other side by a closing mechanism 104, permitting to clip and secure the two portions among them. This setting allows to open and close the blocking element 100 so to easily implant it around a peripheral nerve in order to engage and firmly wrap around or extend about said nerve, in a transverse plane thereto, without damaging the nerve trunk. In an alternative embodiment, the blocking element 100 is composed of a single body element which is slid along a nerve trunk via an access point in the nerve (e.g. in case of an accident-related or surgically severed nerve).

Thanks to its shape, blocking element 100 defines a bore or through-cavity 300 having sufficient size to receive a nerve trunk, with the bore or through-cavity having an axis extending in the direction of extension of the nerve trunk traversing the bore or through-cavity. The cavity 300 can have any suitable shape such as round, squared, rectangular or elliptic as long as it accommodates a nerve trunk and allows the structure of the blocking element 100 to firmly wrap the nerve upon implant in a subject. As will be evident, the dimension of the cavity 300 can vary with the nerve, while its length depends on the number of electrodes that has to be adopted for the specific application (direct proportional relation), as will be detailed later on. As a way of example, for implant in the median nerve, the blocking element 100 should have a cavity 300 of 10 mm.times.1.5 mm.

The upper surface 101 comprises at least one, but preferably a plurality of openings 500, also referred to herein as "access point(s)", while the bottom surface 102 comprises at least one opening 501 referred to herein as "exit point". Being on opposed surfaces, the access points 500 and the exit points 501 are also opposed among them, preferably but not exclusively in a specular fashion. Openings 500 and 501 are disposed relative to bore or through-cavity 300 so as to define an electrode-insertion or -penetration direction oriented at least partially orthogonally to the direction of extension of the nerve bundle through the bore or through-cavity and represent the way through which an elongated electrode 200 can traverse the blocking element 100 in the insertion or penetration direction and through the bore or through-cavity 300 in order to establish an electric contact with the nerve's structures. Said electrode has a distal end 200a, a proximal end 200b and an elongated body 200c. In the frame of the present disclosure, the elongated body 200c represents the length of the body of the electrode 200 intended to span the entire thickness of the element 100 (i.e. within the cavity 300 of the device).

For the sake of clarity, the wording "distal" and "proximal" refers to the distance between the portion of the electrode at stake and an external device to which the electrode is operably connected to e.g. deliver an electric current. The wording "operably connected", "operably connectable", "operably connecting" or even "operably disposed" is used herein to reflect a functional relationship between two or more components of a device or a system, that is, such a wording means the claimed components must be connected in a way to perform a designated function. The "designated function" can change depending on the different components involved in the connection; for instance, the designated function of electrodes operably connected to an electrostimulator is to deliver electric current into a nerve fascicle in order to electrically stimulate it. A person skilled in the art would easily understand and figure out what are the designated functions of each and every component of the device or the system of the invention, as well as their correlations, on the basis of the present disclosure.

The blocking element 100 can be composed of any suitable dielectric or insulating, biocompatible material such as parylene, polyimide, alumina, zirconia or combinations of the foregoing. For assuring a stable contact with a peripheral nerve, in preferred embodiments the blocking element 100 has a rigid or semi-rigid nature, i.e. it cannot or minimally adapt its shape when implanted in a subject.

Turning back to the electrodes 200, the implant device 1 of the invention envisages at least one and preferably a plurality of such electrodes having an elongated shape such as a needle, tubular, conical, pyramidal or cable shape in order to traverse the blocking element 100 entirely along its thickness. In some embodiments, the distal end 200a can have a sharp appearance to facilitate the insertion through the nerve's structures, but a blunt or a round shaped distal end 200a can also be envisaged. Also, needle and thread can be connected to the electrode 200 and guide it.

Electrodes 200 are composed of an electrically conductive portion 201 coaxially disposed within an insulating portion 202 that electrically isolate the conductive portion 201 from the surrounding environment, at least along all the length of the elongated body 200c. The conductive portion 201 can be preferably made of common conductive materials such as metals or alloys compatible with the human body (gold, platinum, activated iridium, platinum-iridium alloy, platinum oxide, iridium oxide, titanium nitrite, rhenium, titanium and the like), conductive polymers, carbon or combinations thereof. The insulating element 202 can be for instance parylene, polyimide, alumina, zirconia and any other suitable insulating material which is biocompatible with the human body. Typically, electrodes 200 have an elongated body 200c comprised between 2 and 20 mm in length and a cross-section comprised between 10 and 1000 µm, depending on the applications and the targeted nerve. Microlithography and/or micro-integrated electronics, among other techniques readily available in the art, can be adopted to fabricate the components of the electrodes.

On the electrode 200 and preferably on the elongated body 200c, an active site 203 is present, allowing the electrical connection between the conductive portion 201 of the electrode 200 and the surrounding environment (i.e. a nerve). The active site 203 is in one embodiment an isolation-free spot, i.e. a portion of the electrode in which the insulating coating 202 is not present or has been removed during the manufacturing process, thus permitting the direct or indirect current passage from the conductive portion 201 to a nerve. The active site 203 can have any suitable size and shape, such as round, squared and so on, or can be a stripe of exposed conductive material. By exploiting this configuration of the active sites present in the electrodes, these latter can be inserted and fixed at the desired profundity within a peripheral nerve so to place the active site(s) in specific target position(s).

Alternatively, the active site 203 can be a protrusion of the conductive portion 201 bulging from the insulating coating 202. In a still alternative embodiment, the active site 203 is an additional conductive element placed in physical contact with the conductive portion 201 and protruding through the insulating portion 202 towards the nerve. In this arrangement, by providing an incision along the insulating portion 202 along the elongated body 200c, the additional conductive element can be possibly displaced along the elongated body 200c so to tailor the position of the active site within the nerve's thickness.

Electrodes' 200 spacing in an array setting may vary. The spacing of the electrodes 200 would be from approximately 100 µm to on the order of 2000 µm in the 3 dimension of the space, depending on the desired density of electrical contact with a nerve.

Figure 2:
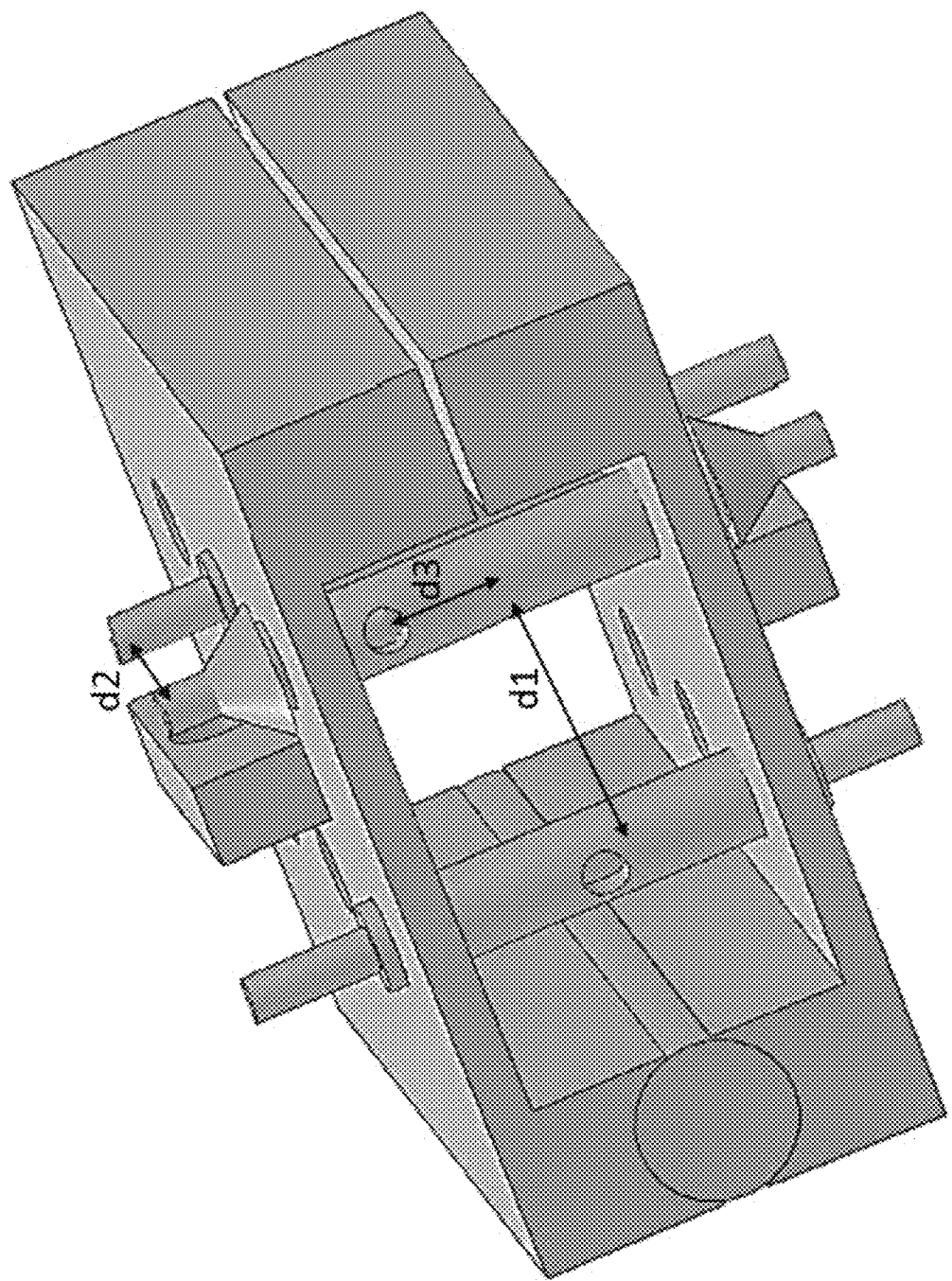

In preferred embodiments of an array setting, the active site's 203 size and inter-spacing (i.e. in the transversal section of the nerve, and in the direction perpendicular to such section) has to be inversely varied, in order to maintain selectivity. In particular, the bigger is the surface of the active sites 203, the less should be the electrodes' 200 density (number). In an embodiment of the invention, the area of the active site 203 is $20 \times 10^{-3}$ mm$^2$ and the distance between the electrodes 200 is 500 µm in the 3 space directions (d1, d2, and d3, FIG. 2).

Figure 3:
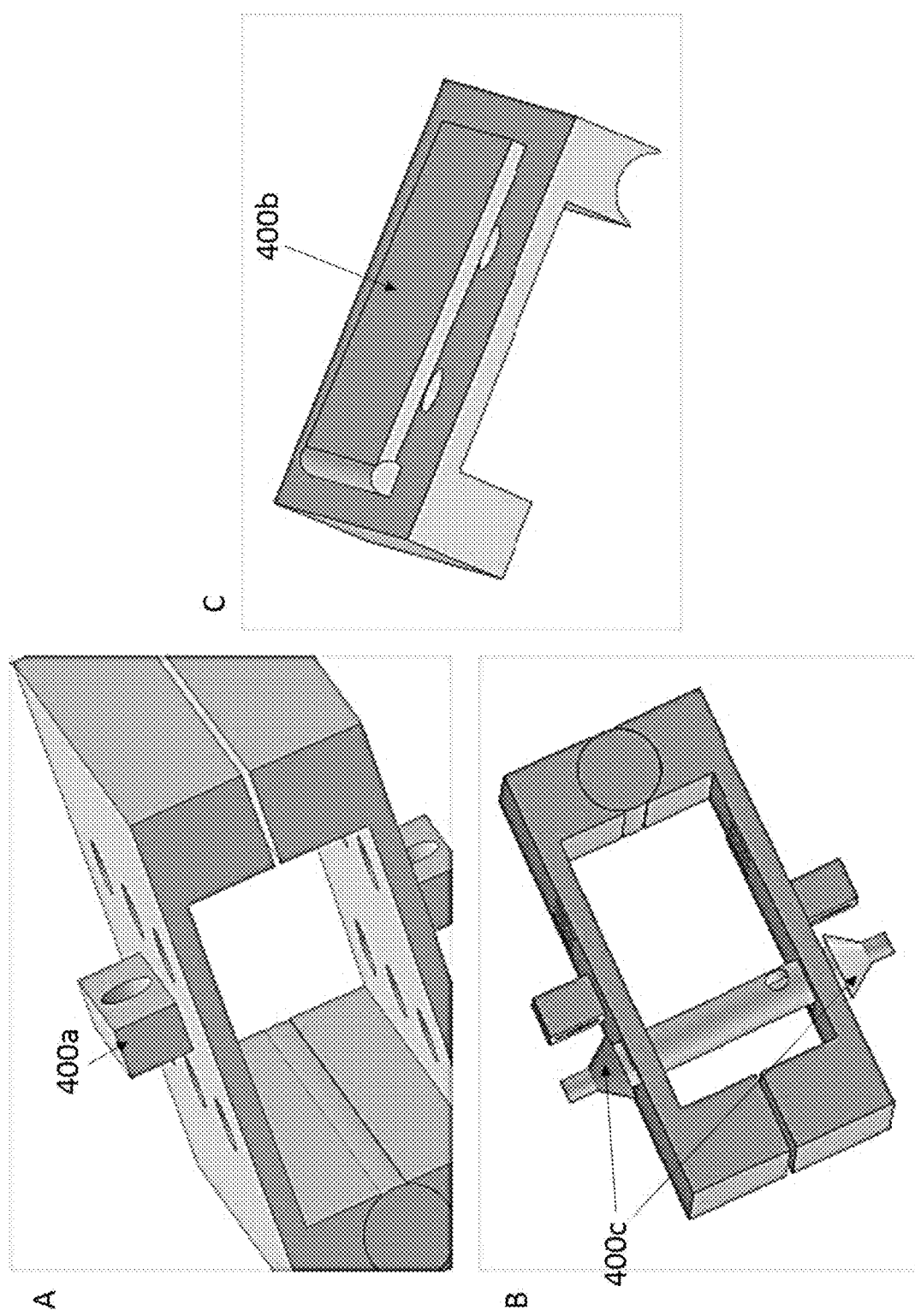
FIG. 3 shows three embodiments concerning means for fixing elongated electrodes to the blocking element, according to another aspect of the invention.

With reference to FIG. 3, some suitable mechanisms for fixing electrodes 200 to the blocking element 100 are shown. In the shown embodiment, electrodes 200 are depicted as cable electrodes. In one scenario, on the upper surface 101 and bottom surface 102 of the blocking element 100 a protuberance 400a comprising a bore is placed or manufactured where the cables 200 should be fixed, in proximity of the access points 500 and exit points 501 (FIG. 3a). Alternatively, a panel 400b constraining the upper surface 101 and bottom surface 102 of the blocking element 100 with a hinge, is pushed on the blocking element 100 itself and sutured, in order to fix the cables 200 once they have been inserted through access points 500 and exit points 501 (FIG. 3b).

In still an alternative embodiment shown in FIG. 3c (see also FIG. 2), the cables 200 are designed with two intrusions 400c, above and below the active site 203 at the level of the distal end 200a and proximal end 200b, which enable their fixation once passed through access points 500 and exit points 501 of the blocking element 100. The two intrusions 400c and the two access points 500 and exit points 501 of the blocking element 100 are designed with different dimensions and/or shapes, in order to avoid a fixation of the cable 200 when only one intrusion has passed the blocking element 100 (and hence no active site 203 has). In an embodiment of the invention, the first intrusion is shaped so that it constraints pulling, while the other pushing. In another embodiment, one couple of intrusion and access point is smaller than the other. In an embodiment of the present invention, the three mechanisms above described can be used in any combination.

Another aspect of the present invention relates to a system for intrafascicular stimulation and/or sensing of a peripheral nerve comprising the device 1 of the invention operably connected with an external device such as an electrical stimulator and/or an analyser. In this context, the electrode can be used to record neural activity from the nerve and/or to stimulate efferent or afferent axons, in order to induce a muscle contraction or a sensation (sight, touch, proprioception, etc.). The electrodes 200 can be connected to a connector that enables at its turn the connection with an implantable or external device. Alternatively, the cables can be soldered directly to an implantable or external device. The system can include additional components such as e.g. a mechanical or electromechanical device that can position with micrometer-scale precision the electrodes in the nervous tissue, in order to find, optimize, and track the electrical signals generated by individual fascicles within a peripheral nerve. An example of such additional component can be, mutatis mutandis, the robotic microdrive described by Wolf et al., *The International Journal of Robotics Research*, vol. 28 no. 9, 1240-1256, 2009, this publication being herewith incorporated by reference in its entirety.

The device 1 of the invention and the associated system can be used in many applications related to peripheral nerve pathological conditions including sensory feedback, motor feedback and erection restoration.

For instance, in an embodiment of the invention, the external device is a neurostimulator implanted in any suitable body part of a subject such as a limb (e.g. a leg) and is wired to the electrodes 200 that are inserted in a nerve. The nerve stimulation can be wirelessly driven by a controller external to the body, transducing the readout of a sole sensor fitted into a shoe under the foot into stimulation parameters. This arrangement, restoring sensory feedback from the foot sole, enables diabetic people to correctly walk and to cure ulcers, avoiding amputation. Indeed, the main cause of foot ulcers is abnormal gait due to loss of sensitivity under the foot sole, caused by the degeneration of the nerve endings located in the foot.

The invention claimed is:

1. An implantable device for intrafascicular stimulation and/or sensing of a peripheral nerve, comprising:
   a) a blocking element adapted for wrapping around or extending about, and in a transverse plane to, a nerve extending in a first direction, said blocking element defining a bore or through-cavity having an axis extending in said first direction, said blocking element comprising at least one access point and at least one exit point disposed relative to said bore or through-cavity so as to define a second direction oriented at least partially orthogonally to said first direction; and
   b) an electrode adapted to entirely traverse, in said second direction, the blocking element and said bore or through-cavity via the at least one access point and the at least one exit point, said electrode having a distal end, a proximal end and an elongated body in between, said electrode being electrically isolated from a surrounding environment except that for an active site.

2. The device of claim 1, wherein the active site is located along the elongated body.

3. The device of claim 1, wherein the active site is an isolation-free spot or a strip.

4. The device of claim 1, wherein the blocking element is openable and closable.

5. The device of claim 1, wherein the electrode is a cable electrode.

6. The device of claim 1, further comprising means for fixing the electrode to the blocking element.

7. The device of claim 1, wherein the active site can be displaced along the elongated body.

8. A system for intrafascicular stimulation and/or sensing of a peripheral nerve comprising the device of claim 1 operably connected with an electrical stimulator and/or an analyzer.

* * * * *